US00PP27636P3

(12) United States Plant Patent
Paduch

(10) Patent No.: US PP27,636 P3
(45) Date of Patent: Jan. 31, 2017

(54) ***RHIPSALIDOPSIS* PLANT NAMED 'BEVERLY'**

(50) Latin Name: ***Rhipsalidopsis* hybrid**
Varietal Denomination: Beverly

(71) Applicant: Louis Paduch, Carver, MA (US)

(72) Inventor: Louis Paduch, Carver, MA (US)

(73) Assignee: Bay City Flower Co., Half Moon Bay, CA (US)

( * ) Notice: Subject to any disclaimer, the term of this patent is extended or adjusted under 35 U.S.C. 154(b) by 42 days.

(21) Appl. No.: 14/121,392

(22) Filed: Aug. 29, 2014

(65) Prior Publication Data

US 2016/0066494 P1 Mar. 3, 2016

(51) Int. Cl.
*A01H 5/02* (2006.01)

(52) U.S. Cl.
USPC ..... Plt./372

(58) Field of Classification Search
USPC ..... Plt./372
See application file for complete search history.

*Primary Examiner* — Annette Para
(74) *Attorney, Agent, or Firm* — James R. Cypher; Charles R. Cypher

(57) ABSTRACT

A variety of the Cactaceae family produced by a controlled cross named 'Bevely'. 'Beverly' has a strong growth habit, a "red" colored bloom, a strong propensity to branch with minimal pruning, erect stems, and blooming flowers that last for two weeks on the plant.

3 Drawing Sheets

Latin name of genus and species of the plant claimed: *Rhipsalidopsis* hybrid.

Varietal denomination: The new plant's varietal denomination is 'Beverly'.

BACKGROUND OF THE INVENTION

The present invention relates to a new and distinct variety of the Cactaceae family. The new variety is a *Rhipsalidopsis* hybrid named 'Beverly' by the inventor. The inventor is Louis Paduch, a citizen of the United States.

SUMMARY OF THE INVENTION

This new variety was produced by the inventor through a controlled hybridization process from commercial varieties. The parent plants have not been patented or otherwise formally identified.

The overall red appearance of the flower is due to the generally even-toned color of its tepals.

The distinguishing characteristics of the new variety are retained by asexually reproduced, successive generations.

The new variety possesses the desirable characteristics of: a strong growth habit with erect stems; a "red" colored bloom—RHS 46B (red group); relatively large flowers; and a strong propensity to branch with minimal pruning.

Blooming flowers on the plant can last as long as two weeks at temperatures between 60 and 70 degrees Fahrenheit. Cold temperatures slow down the rate at which buds mature into flowers. Strong light is also necessary for bud development.

TABLE 1

| | New Variety 'Beverly' | U.S. Plant Pat. No. 26,473 Rhipsalidopsis plant named 'PKMRHIP-S09' | U.S. Plant Pat. No. 14,423 Rhipsalidopsis Plant named 'Lauren' | U.S. Plant Pat. No. 21,717 Rhipsalidopsis Plant named '7371E' |
|---|---|---|---|---|
| Plant height | 8" to 9" | 13 to 15 cm | 12 cm | 16 cm |

TABLE 1-continued

| | New Variety 'Beverly' | U.S. Plant Pat. No. 26,473 Rhipsalidopsis plant named 'PKMRHIP-S09' | U.S. Plant Pat. No. 14,423 Rhipsalidopsis Plant named 'Lauren' | U.S. Plant Pat. No. 21,717 Rhipsalidopsis Plant named '7371E' |
|---|---|---|---|---|
| Phyllo-clades | 40-60 mm long, 13-30 mm wide, color RHS 137A (green group). | 25-35 mm long, up to 24 mm wide, color RHS 146A (yellow-green group). | 20-55 mm long, up to 19 mm wide, color RHS 137C. | 3-4 cm long, 2-3 cm wide, color RHS 147A (yellow group). |
| Flower | Diameter: 5.5 cm. | Diameter: up to 7 cm. Length: 4 cm, including ovary. | Diameter: 31-38 mm. | Diameter: 3-4 cm. Length: 4-5 cm , including ovary |
| Telaps | Up to 4 cm long, color RHS 46 B (red group) | Up to 35 mm long, up to 7 mm wide, color RHS 34 A (orange-red group) | 19-25 mm long, color RHS 69 A (red-purple group) | 2.8-3.0 cm long, 6-8 mm wide, color RHS 31 B (orange-red group) |
| Filament Color | RHS 74 B (red-purple group) | RHS N155C-N155D | "darker than perianth" | RHS N155D |

The new variety has asexually reproduced by the inventor and under the direction of the inventor at a commercial nursery in Half Moon Bay, Calif. The new variety has been asexually reproduced through successive generations by cuttings, and it has been found that the combination of characteristics as herein disclosed remain firmly fixed.

BRIEF DESCRIPTION OF THE DRAWING

The accompanying drawings serve, by color photographic means, to illustrate the new plant variety. The colors are represented as truly as possible using conventional photographic procedures.

DETAILED DESCRIPTION OF THE NEW VARIETY

Figure 1:
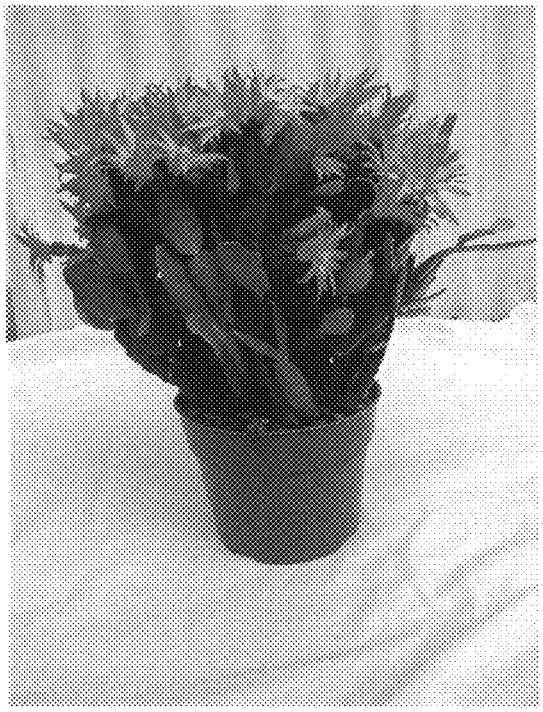
FIG. 1 is a color photograph of several individuals of the new variety illustrating the overall appearance and form of the plants, and the abundance of blooms, when grown in a single pot for commercial sale.
Figure 2:
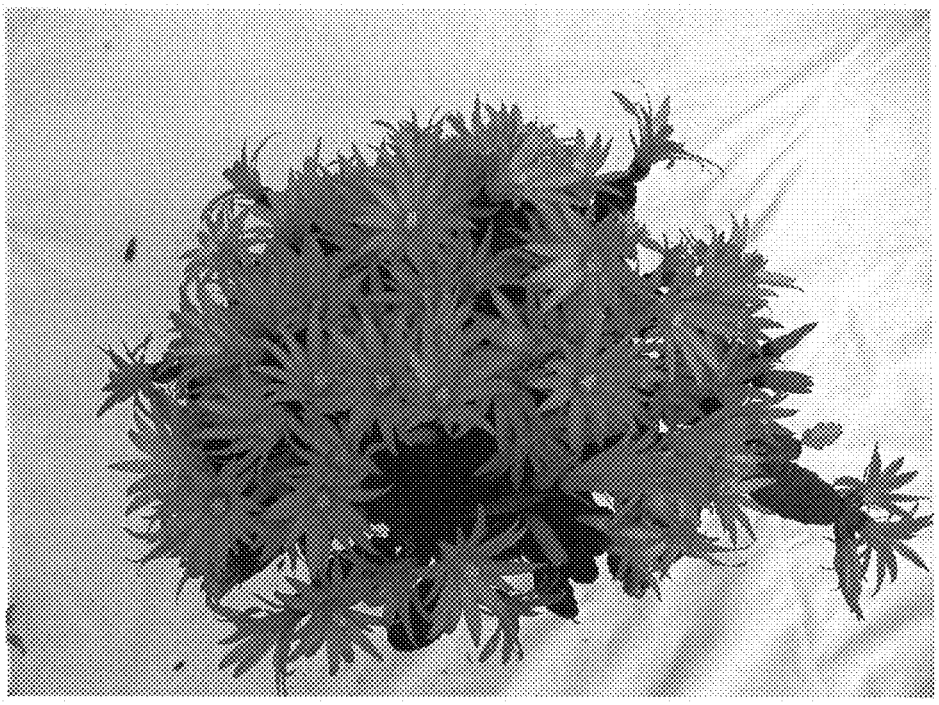
FIG. 2 is a color photograph of several individuals of the new variety illustrating the overall appearance and form of the plants, and the abundance of blooms, when grown in a single pot for commercial sale.
Figure 3:
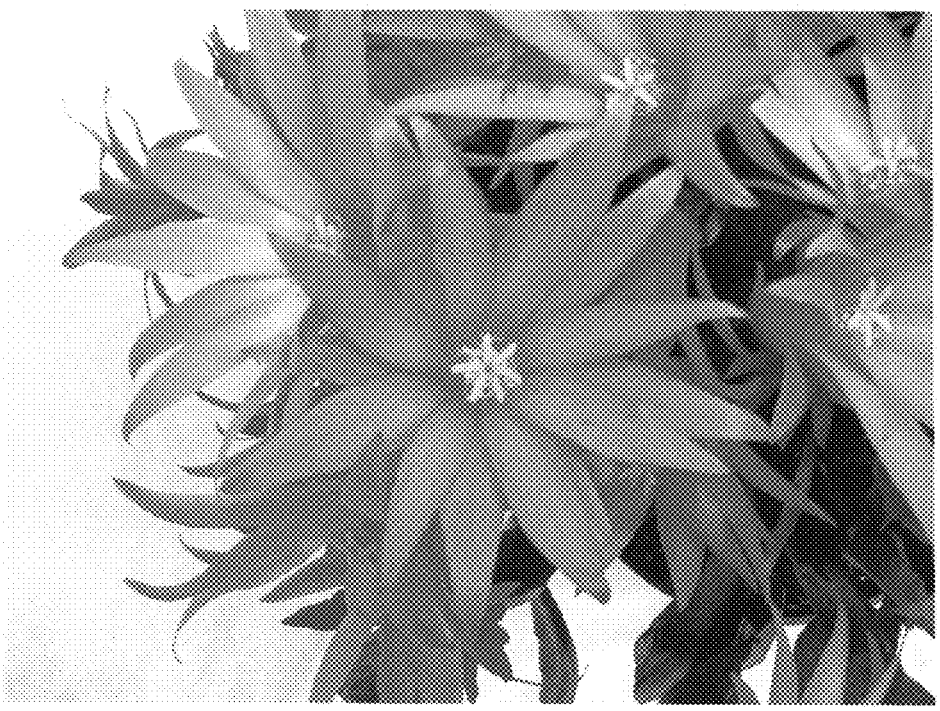
FIG. 3 is color photograph of a several flowers of the new variety.
Figure 4:
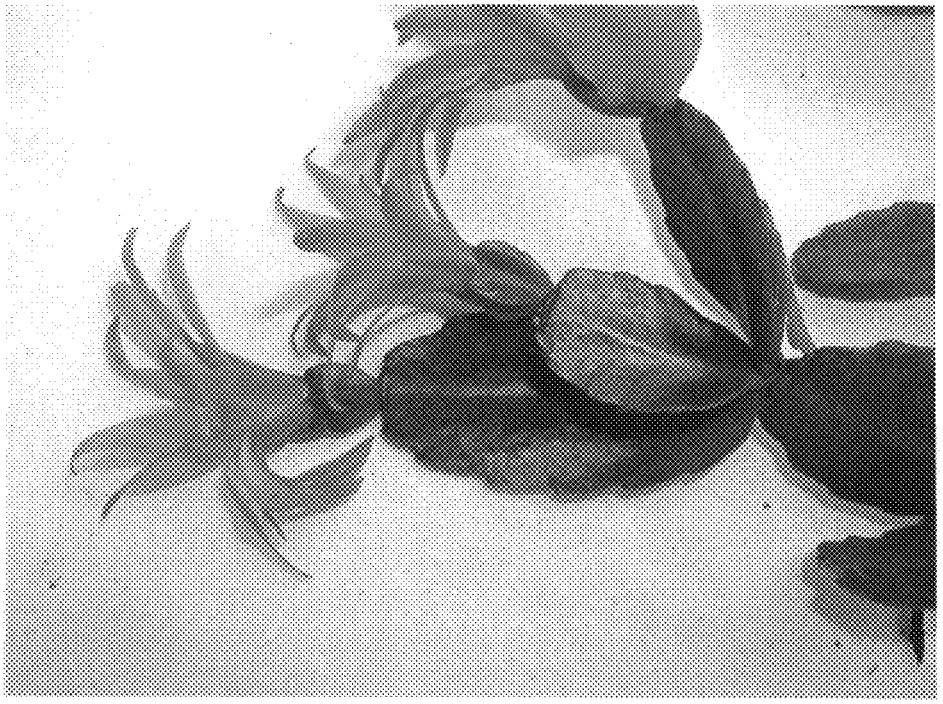
FIG. 4 is a color photograph of the top of a flowering stem of the new variety.
Figure 5:
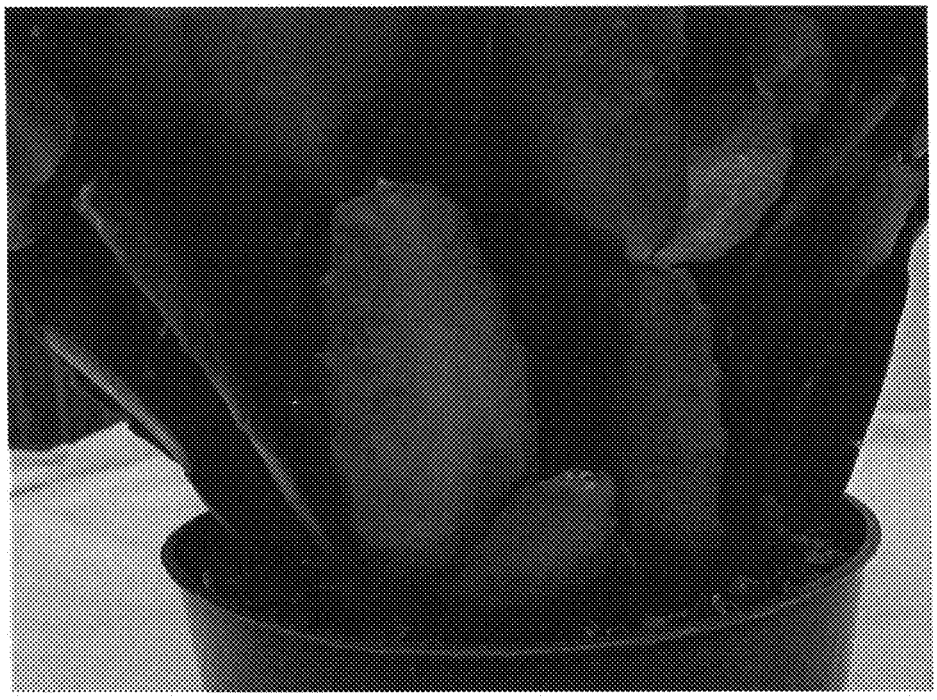
FIG. 5 is a color photograph of the base of several plants of the new variety.
Figure 6:
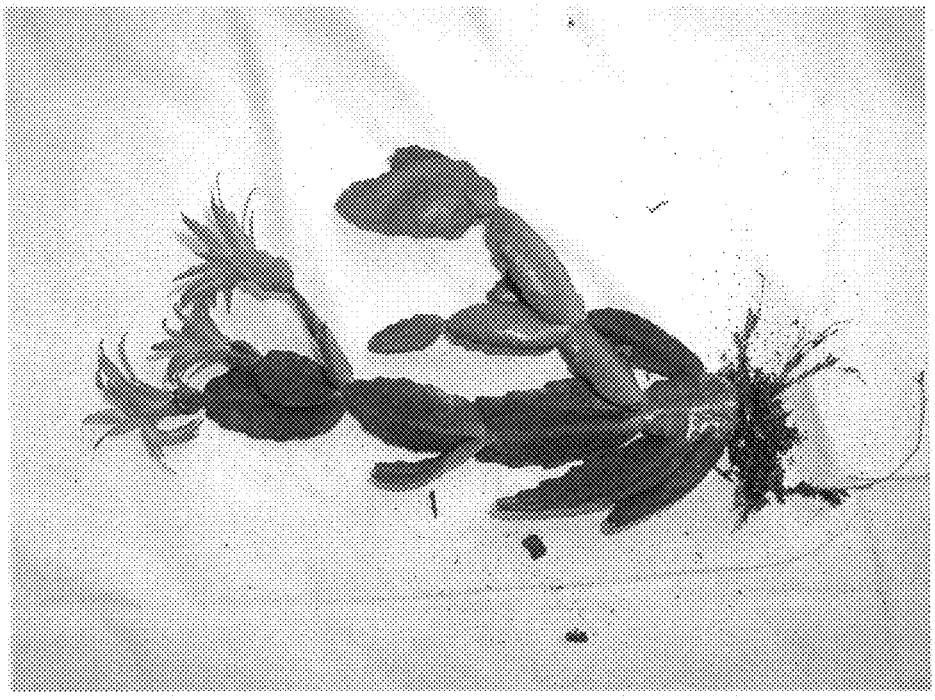
FIG. 6 is a color photograph of one individual plant grown for commercial sale removed from its soil.

The following is a detailed description of the new variety. The new variety has not been observed under all possible environmental conditions. Color designation and other values may deviate slightly from the stated values from flowering to flowering, but the deviations will be within the range expected from varying environmental, seasonal and cultural conditions. Color designations were made according to The R.H.S. Colour Chart published by The Royal Horticultural Society of London, England.

The plants observed were grown in 6" pots. The observed plants are ready for commercial sale.

The plants observed had been pruned back once. There were typically 6 or 7 cuttings placed in each pot. Some cuttings had five levels of phylloclades, including the basal phylloclade that was inserted in the dirt, with buds at the top of the highest phylloclades. Most other plants had 4 levels of phylloclades with buds growing on the highest phylloclades.

The following description is based on observations of optimally fertilized plants.

The plants were started in green houses at a commercial nursery in Half Moon Bay, Calif. Temperatures in Half Moon Bay on average range from 55 to 65 degrees Fahrenheit in the summer months, and from 45 to 55 degrees Fahrenheit in the winter months.

The plants started as cuttings taken as entire phylloclades. Cuttings were dried in flats for four weeks to harden. 6 to 7 cuttings were then placed in the same pot. The cuttings were kept under glass while they were rooting. At night, the plants were kept at an average temperature of approximately 64 degrees Fahrenheit, and during the day, the plants were allowed to get as hot as 75 to 80 degrees Fahrenheit. Cuttings generally take a month to begin producing roots and then another month to fully root.

When the plants were between five and eight months old, when the new variety had produced three new levels of phylloclades, the top phylloclades were topped or broken from the stems by twisting.

Then, when plants were at an appropriate height for commercial sale, the plants were moved outside to be exposed to colder temperatures for at least two months. Under the conditions in Half Moon Bay, the exposure to colder temperatures initiates bud formation without having to keep them under glass where day length can be shortened.

DETAILED PLANT DESCRIPTION

Varietal name: 'Beverly'.

Classification: Family—Cactaceae.

Genus and species: *Rhipsalidopsis* hybrid.

Parentage: Un-named individuals that are also *Rhipsalidposis* hybrids.

Form: Terrestrial, shade-loving, succulent, leafless plant with jointed and branched stems.

Stems:

*General*.—Irregular stems of multi-branching upright, adventitiously rootable, flattened phylloclades. Plants observed had stems that generally consisted of 4 levels of phylloclades, and sometimes 5. There stems branch at multiple levels, usually with 1 to three branches growing out of the apex of the phylloclade. The flattened phylloclades have a fairly prominent midrib (especially in phylloclades at the base of mature plants) and weakly toothed lateral wings. The observed plants were 8" to 9" high.

Phylloclades:

*General*.—Mature phylloclades are generally oblong, elongated, and flattened with wings, and have a transversely elongated, areole bearing, truncated apex. From the transversely elongated apex, the wing margins generally run straight or taper slightly to the basal portions (or occasionally they flare outwardly somewhat), where they then taper and merge through a pointed, basal juncture with the phylloclade therebelow. The margins of the wings are also weakly toothed or weakly crenate and an axillary areole is associated with each blunt tooth. Immature phylloclades are often not flattened, but four-angled, having multiple ribs terminating at axillary areoles. The apex of the phylloclade is transversely elongated, and areole bearing with compound areoles. The lateral margins typically have 4 to 5 alternately spaced axillary areoles.

*Midrib*.—A somewhat prominent midrib extends longitudinally of the phylloclade and continuously through the joints.

*Texture*.—Phylloclades have a smooth, waxy epidermis. Wax in basal phylloclades and phylloclades inserted in the ground becoming thick, corky and translucent with age. First phylloclade above basal phylloclade will often have thick corky wax at its base and along up its midrib part way.

*Size*.—Phylloclades are usually between 40 mm and 60 mm long, with some as short as 20 mm. Phylloclades bearing flowers can be as short as 32 mm long. Phylloclades are generally 4 mm thick at the midrib, and tapering to 1 mm thick at the margins. Phylloclades are generally 13 to 30 mm at their widest point.

Color: Mature phylloclades are RHS 137A while immature phylloclades are a brighter green: RHS 152C. Some phylloclades can have dark margins, with the midrib and base of the phylloclade being lighter.

*Areoles*.—Terminal areole — Large, compound, elongated, oval-shaped with several acicular bristles, copious multi-cellular hairs, and several buds that may mature into either new phylloclades or flowers.

The opposite ends of the areole are located adjacent to subsidiary areoles which are in turn located at the axils of the uppermost blunt teeth located at the distal end of the of phylloclade. The acicular bristles are mostly upright (some bent) bristles in clumps which can be as long as 5 mm and as short as 2 mm. Lateral margins of phylloclade at terminal areole exposed to sun can be very red. Axiallary areoles — Typically there are 4 axial areoles on one side of the phylloclade and five on the other, with the areoles alternating. Typically these areoles have 3 to 4 acicular bristles without glochidia, especially in the upper areoles. Uppermost axiallary areoles also have short hair. Bristles of the axiallary areoles are often shorter than the bristles of areole at the apex of the phylloclade. Blunt teeth are also found with the axiallary areoles.

Buds:

*General*.—Unarmored and ovid. Color of tepals of buds are generally RHS 46 A (red group). From 1 to 6 flower buds can form on the elongated terminal areole of the uppermost phylloclades. Most of the buds on the uppermost phylloclades will fall of the plant before the flowers bloom; however, when the plant is in full bloom it is common for the uppermost phylloclade to have 2 or more buds of different sizes and age, often with 2 being of similar age and opening simultaneously. Some buds growing in the first axiallary areole. Some buds will also form on the second highest phylloclade of a branch, sometimes as many as three, but more typically 1 or 2.

Flowers:

*General*.—Sessile, actinomorphic, terminal, perfect and epigynous with tepals (undifferentiated whorled sepals and petals) having a spiral emergence as a perianth. Perianth, androecium and gynoecium separate easily from ovary when pulled from the ovary, but if undisturbed will wither attached to the ovary.

*Perianth*.—General: Free, whorled tepals inserted on top of the ovary. Tepals become more reflexed as the flower ages. When the flower is mature there are often 5 very small sepals whose color ranges from RHS 46 A (red group) to RHS 175 B (greyed-orange group). As many as 20 tepals on a flower. Shape: Lanceolate with entire margins and very acute tips. Texture: Glabrous. Size: Largest tepals of mature flower is 4 cm. Fully opened flower generally has a diameter of 5.5 cm. Color: Tepals are thin. Tepals are uniformly dark above base on both sides. Overall color appearance of tepals is RHS 46 B (red group). Some tepals are become RHS 54 B (red group).

*Androecium* (*stamens*).—General: Numerous stamens (often more than 70) with outermost stamens having filaments basally fused to the perianth. Filaments are basally attached to the anther. Stamens are inserted with respect to the sepals, but become exserted as the tepals become reflexed. Color: Filaments are mostly RHS 74B. Pollen color: RHS 21A. Texture: Filament is glabrous. Size: Stamen filaments s are approximately 10 to 20 mm long, and the anthers are approximately 1 mm long.

*Gynoecium* (*pistil*).—General: Compound ovary with parietal placentation (generally 5 carpels), having a united style, that is of equal length as stamens, and inserted in tepals, but becoming exserted as tepals become reflexed. Style: RHS 158C (yellow-white group) at base with RHS 73C (red-purple group) portions. Length: 16 mm. Texture: glabrous. Stigma: Erect and become reflexed as it ages with usually 6 lobes (but there can be as many as 8 lobes) Color: RHS 158 C (yellow-white group) on the abaxial side.

*Ovary*.—General — Compound ovary with a single cavity and parietal placentation and generally 5 carpels, with numerous ovules. The ovary is inferior and obovate to terete with five angles and generally broadening from insertion to floral end. Generally, mature ovaries have a diameter of about 7 mm. Color — RHS 147 B (yellow-green group).

Bloom life: Two to three weeks when forced.

Fruit: General: ovaries wither and fall from phylloclades with flower.

I claim:

1. The new and distinct hybrid plant of the Cactaceae family substantially as herein shown and described.

* * * * *